(12) United States Patent
Imai

(10) Patent No.: US 9,155,679 B2
(45) Date of Patent: Oct. 13, 2015

(54) MEDICAL CONTAINER AND SYRINGE

(75) Inventor: Masaomi Imai, Nakakoma-gun (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 761 days.

(21) Appl. No.: 13/265,522

(22) PCT Filed: Mar. 26, 2010

(86) PCT No.: PCT/JP2010/055315
§ 371 (c)(1),
(2), (4) Date: Oct. 20, 2011

(87) PCT Pub. No.: WO2010/122872
PCT Pub. Date: Oct. 28, 2010

(65) Prior Publication Data
US 2012/0053529 A1    Mar. 1, 2012

(30) Foreign Application Priority Data
Apr. 21, 2009  (JP) .................. 2009-103182

(51) Int. Cl.
*A61M 37/00* (2006.01)
*A61J 1/20* (2006.01)
*A61M 5/315* (2006.01)
(Continued)

(52) U.S. Cl.
CPC .............. *A61J 1/2089* (2013.01); *A61J 1/2037* (2015.05); *A61M 5/31596* (2013.01); *A61J 1/10* (2013.01); *A61J 1/2096* (2013.01); *A61M 5/282* (2013.01); *A61M 5/3148* (2013.01); *A61M 2005/31516* (2013.01); *A61M 2005/31598* (2013.01)

(58) Field of Classification Search
CPC ................... A61M 5/282; A61M 2005/31598; A61M 5/2425
USPC ...................... 604/82–91, 185, 212
See application file for complete search history.

(56) References Cited

U.S. PATENT DOCUMENTS 2,514,575 A * 7/1950 Hein et al. .................... 604/202
4,131,217 A * 12/1978 Sandegren ....................... 222/82
(Continued)

FOREIGN PATENT DOCUMENTS

| EP | 0 505 611 A2 | 9/1992 |
| GB | 2 253 387 A | 9/1992 |
| JP | 2006-055452 A | 3/2006 |

OTHER PUBLICATIONS

International Search Report (PCT/ISA/210) issued on Jun. 29, 2010, by Japanese Patent Office as the International Searching Authority for International Application No. PCT/JP2010/055315.
(Continued)

*Primary Examiner* — Emily Schmidt
(74) *Attorney, Agent, or Firm* — Buchanan Ingersoll & Rooney PC

(57) ABSTRACT

A syringe is provided with an inner tube which has at the tip thereof a mouth section through which liquid can enter and exit the inner tube; a bag body which is disposed inside the inner tube and is flexible and reversible; a gasket which is mounted to the tip of the inner tube; and an outer tube in which the inner tube is inserted together with the gasket so as to be movable in the axial direction. The syringe is configured in such a manner that, when liquid enters and exits through the mouth section, the bag body is reversed to change the volume of a containing space surrounded by the inner tube and the bag body.

17 Claims, 8 Drawing Sheets

(51) Int. Cl.
*A61J 1/10* (2006.01)
*A61M 5/28* (2006.01)
*A61M 5/31* (2006.01)

(56) References Cited

U.S. PATENT DOCUMENTS

| | | | | |
|---|---|---|---|---|
| 4,236,516 A | * | 12/1980 | Nilson | 604/214 |
| 4,312,344 A | * | 1/1982 | Nilson | 604/212 |
| 4,581,016 A | * | 4/1986 | Gettig | 604/88 |
| 4,861,335 A | | 8/1989 | Reynolds | |
| 5,891,102 A | * | 4/1999 | Hiejima et al. | 604/185 |
| 6,083,204 A | * | 7/2000 | Malerba et al. | 604/181 |
| 6,213,981 B1 | * | 4/2001 | Hiejima et al. | 604/185 |
| 2010/0249718 A1 | * | 9/2010 | Ishizaki et al. | 604/185 |

OTHER PUBLICATIONS

Written Opinion (PCT/ISA/237) issued on Jun. 29, 2010, by Japanese Patent Office as the International Searching Authority for International Application No. PCT/JP2010/055315.

\* cited by examiner

MEDICAL CONTAINER AND SYRINGE

TECHNICAL FIELD

The present invention relates to a medical container and a syringe.

BACKGROUND ART

Normally, many medicines are stored in vial containers (medicine-storing containers) each having a mouth section sealed with a rubber plug. As such a vial container, there has been known one which includes a tubular container body having one opening for functioning as a mouth section, a partition wall member which partitions the inside of the container body into a first space and a second space and which is slid inside the container body, and a medicine stored in the first space (see, for example, Patent Document 1).

In the vial container described in Patent Document 1, in the case of extracting, for example, a powdery medicine from the vial container, a mouth section of a syringe in which a dissolving liquid is apportioned is connected to the mouth section of the vial container, and the dissolving liquid is injected. Thereafter, in the condition where the syringe and the vial container are connected with each other, a pumping operation is carried out by a plunger of the syringe to cause the dissolving liquid to enter and exit the vial container, whereby the medicine is dissolved uniformly in the dissolving liquid. Then, the dissolving liquid containing the medicine dissolved therein is extracted by sucking it into the syringe.

When the pumping operation is conducted, however, the partition wall member slides inside the container body, thereby producing a frictional resistance between the partition wall member and the container body. As a result, it becomes difficult to conduct the pumping operation smoothly. In other words, there has been a problem that the above-mentioned vial container is poor in operability during the pumping operation.

Patent Document 1

Japanese Laid-Open Patent Publication No. 2006-055452

SUMMARY OF INVENTION

It is an object of the present invention to provide a medical container and a syringe which are excellent in operability of injecting a liquid therein and discharging a liquid therefrom.

In order to attain the above object, according to the present invention, there is provided a medical container including:

a tube body having, at a distal end portion thereof, a mouth section through which a liquid can enter and exit; and a bag body which is disposed inside the tube body and which is flexible and reversible, wherein when a liquid enters and exits through the mouth section, the bag body is reversed so as to change the volume of a space surrounded by the tube body and the bag body.

In the medical container according to the present invention, preferably, the bag body is reversed with a portion near an intermediate part in the axial direction inside the tube body as a fulcrum.

In the medical container according to the present invention, preferably, the bag body has a bottom section and a side section integrally formed at an edge portion of the bottom section, and when the bag body is reversed, the side section is brought into close contact with a portion of the tube body that is positioned on the distal end side relative to the fulcrum.

In the medical container according to the present invention, preferably, the thickness of the side section is smaller than the thickness of the bottom section and/or the material of the bottom section is harder than the material of the side section.

In the medical container according to the present invention, preferably, a flexible thin section is formed at a boundary section between the bottom section and the side section.

In the medical container according to the present invention, preferably, the bag body has a raised section which is inverted and then enters the mouth section when the liquid flows out through the mouth section.

The medical container according to the present invention, preferably, further includes:

a gasket mounted on the distal end portion of the tube body; and a syringe outer tube in which the tube body together with the gasket is inserted so as to be movable in an axial direction thereof, wherein the space can communicate, through the mouth section, with a distal-end-side space surrounded by the syringe outer tube and the gasket.

In addition, in order to attain the above object, according to the present invention, there is provided a syringe including:

a syringe outer tube;

a gasket which is inserted in the syringe outer tube so as to be movable in an axial direction thereof; and a plunger which is connected to the gasket and is operated to move the gasket, wherein the plunger includes a tube body having, at a distal end portion thereof, a mouth section through which a liquid can enter and exit, and a bag body which is disposed inside the tube body and which is flexible and reversible; and wherein when a liquid enters and exists through the mouth section, the bag body is reversed so as to change the volume of a space surrounded by the tube body and the bag body.

Further, in the medical container according to the present invention, preferably, the bag body has an opening section fixed to an inner peripheral section of the tube body along a circumferential direction thereof.

In addition, in the medical container according to the present invention, preferably, the tube body has at the inner peripheral section a stepped section which varies in inside diameter, and the opening section of the bag body is fixed to the stepped section.

Besides, in the medical container according to the present invention, preferably, the bag body has different colors on the face side and on the reverse side, respectively.

In addition, the medical container according to the present invention, preferably, further includes an opening/closing means for opening and closing the mouth section.

Further, in the medical container according to the present invention, preferably, the opening/closing means has a valve body which is mounted on the mouth section, is made of an elastic material, and has a slit which is opened and closed when necessary.

In addition, the medical container according to the present invention, preferably, includes an opening/closing means for opening and closing the mouth section thereby to switch between communication and non-communication between the space and the distal-end-side space.

Besides, in the medical container according to the present invention, preferably, the opening/closing means has a breakable communicating section which is disposed at the mouth section and provides communication by being broken.

In addition, according to the present invention, there is provided preferably a syringe including:
the medical container according to the present invention;
a gasket mounted on a distal end portion of the tube body; and
a syringe outer tube in which the tube body together with the gasket is inserted so as to be movable in an axial direction thereof.

DESCRIPTION OF EMBODIMENTS

Now, a medical container and a syringe according to the present invention will be described in detail below, based on preferred embodiments shown in the accompanying drawings.

First Embodiment

Figure 1:
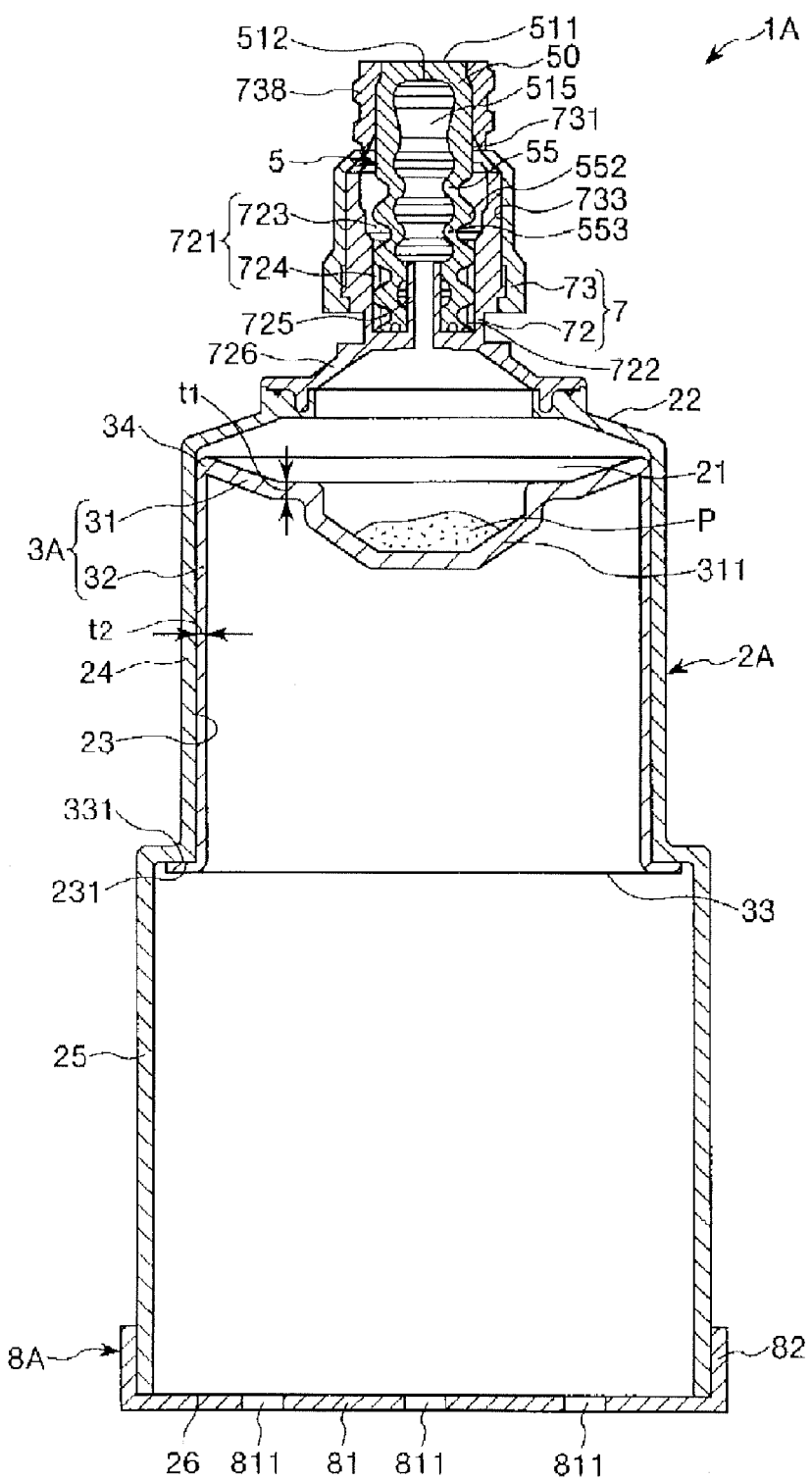
FIG. 1 is a longitudinal sectional view showing an embodiment in the case where a medical container according to the present invention is applied to a vial container.
Figure 2:
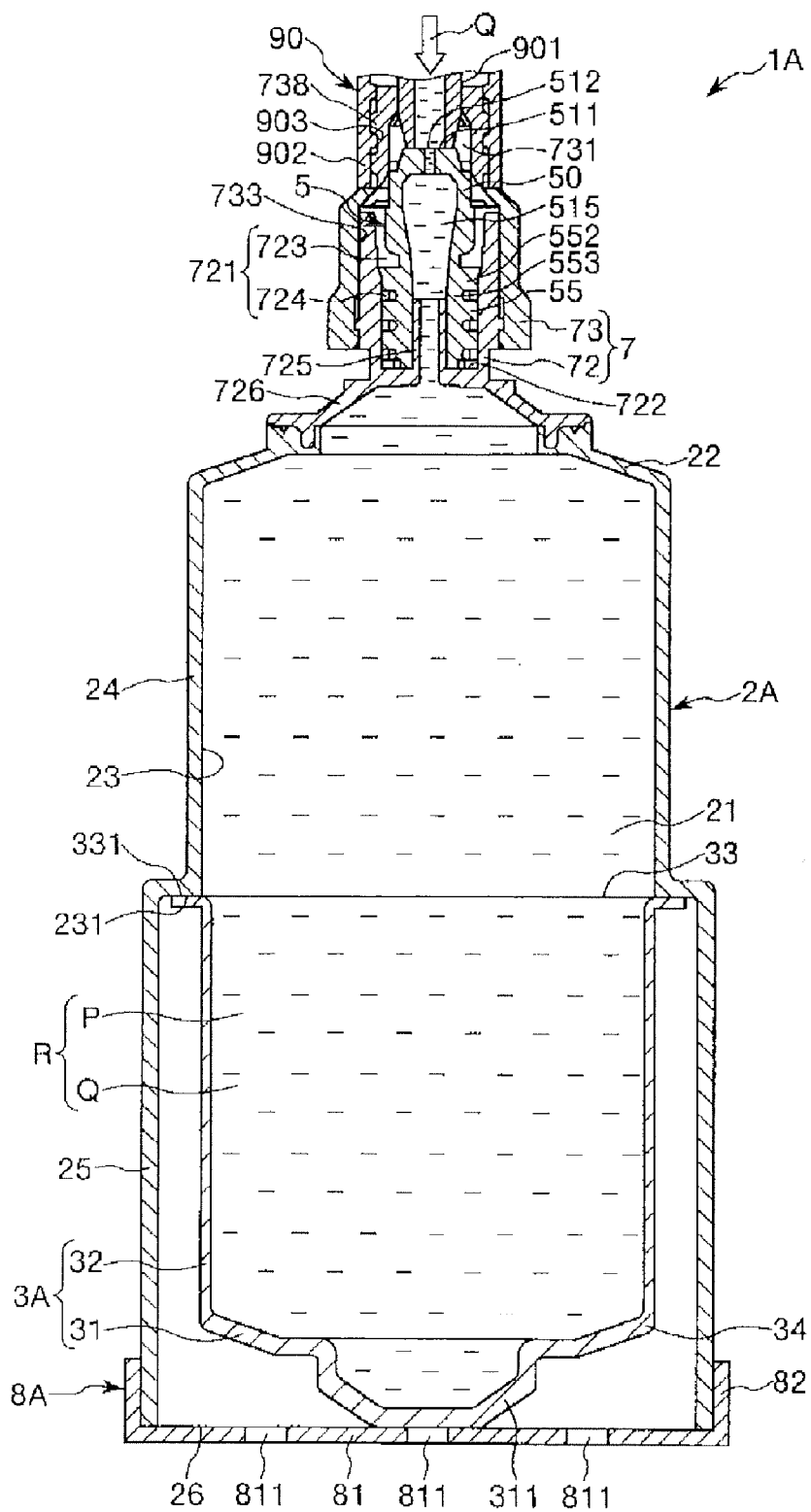
FIG. 2 is a longitudinal sectional view showing the embodiment in the case where the medical container according to the present invention is applied to the vial container.
Figure 3:
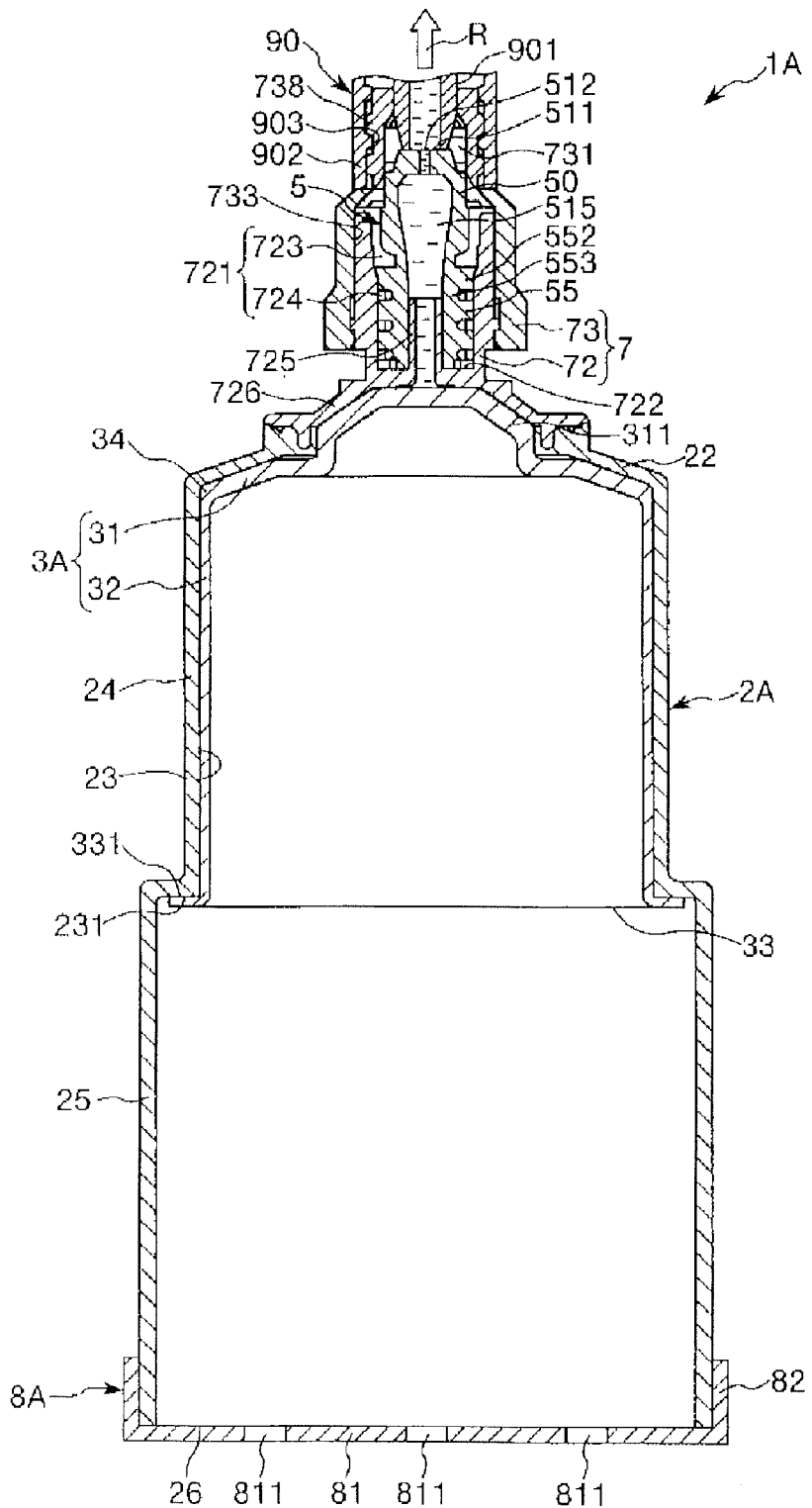
FIG. 3 is a longitudinal sectional view showing the embodiment in the case where the medical container according to the present invention is applied to the vial container.

FIGS. 1 to 3 are longitudinal sectional views each showing an embodiment in the case where the medical container according to the present invention is applied to a vial container. Incidentally, in the following, for convenience of description, the lower side in FIGS. 1 to 3 will be referred to as "proximal end side," and the upper side as "distal end side."

The vial container (medical container) shown in FIGS. 1 to 3 includes a container body (tube body) 2A having a mouth section 7 at its distal end portion, a valve body 5 serving as an opening/closing means for opening and closing the mouth section 7, a bag body 3A disposed in the container body 2A, and a medicine P in the form of powder, liquid or the like (in the present embodiment, in the form of liquid) which is contained in a containing space (space) 21 surrounded by the container body 2A and the bag body 3A.

In the vial container 1A, for example, an operation of injecting a liquid Q such as a dissolving liquid, a diluting liquid, a medicinal solution or the like into the container body 2 through the mouth section 7, to mix the medicine P with the liquid Q is carried out. In the following, the mixture of the medicine P and the liquid Q will be referred to as "a medicinal liquid R." Incidentally, though not specifically restricted, examples of the medicine P include medicines which are dangerous if erroneously touched by a medical worker, such as carcinostatic agents, immunosuppressant, etc., medicines which must be dissolved in use, such as antibiotic, styptic, etc., medicines which need dilution, such as pediatric drugs, etc., and medicines which needs multi-time dispensing, such as vaccine, heparin, pediatric drugs, etc. In addition, though not particularly limited, the liquid Q may be, for example, physiological saline.

Also, the injecting of the liquid Q can be carried out by use of a prefilled syringe 90, for example. As shown in FIGS. 2 and 3, the prefilled syringe 90 includes a syringe outer tube having a mouth part 901 projectingly formed at an end portion thereof, a tubular lock part 902 disposed at an outer peripheral portion of the mouth part 901 concentrically with the mouth part 901, a gasket (not shown) slidable inside the syringe outer tube along the longitudinal direction thereof, and a plunger (not shown) operated to move the gasket. In addition, a space surrounded by the syringe outer tube and the gasket is filled with the liquid Q. The liquid Q is caused to flow out through the mouth part 901 of the syringe outer tube by pushing the plunger.

The structure of the vial container 1A will be described.

The container body 2A has a bottomed tube-like shape, and has a mouth section 7 formed at a bottom section 22 thereof in a projecting manner. The container body 2A is provided at an intermediate part of an inner peripheral section 23 thereof with a stepped section 231 at which the inside diameter is changed abruptly. The stepped section 231 serves as a fixing section at which the bag body 3A is fixed, and also serves as a fulcrum at the time of reversion of the bag body 3A. In addition, the container body 2A can be divided, through the stepped section 231, into a smaller diameter section 24 on the distal end side and a larger diameter section 25 on the proximal end side.

The mouth section 7 is a part through which the liquid Q enters and exits, and in other words, the mouth section 7 forms a flow passage through which the liquid Q passes. The mouth section 7 has an overall outside diameter which is further reduced as compared with the outside diameter of the smaller diameter section 24, and includes a tubular section 72 formed at the bottom section 22 so as to project in the distal end direction, and a cap section 73 mounted on the tubular section 72.

The tubular section 72 has therein a valve body installing section 721. The valve body installing section 721 is divided into a second lumen part 723 and a third lumen part 724 which is positioned closer to the distal end than the second lumen part 723 and is smaller in inside diameter than the second lumen part 723. In addition, the inside diameter of the third lumen part 724 is preferably slightly greater than the maximum outside diameter of a barrel section 55 of the valve body 5 which will be described later.

Further, an inside projection 725 composed of a tube-like body is provided at a central portion of a bottom surface 722 of the tubular section 72. As shown in FIGS. 2 and 3, when the valve body 5 starts being pushed, the inside of the valve body 5 is supported by the inside projection 725, whereby it is possible to prevent the valve body 5 from buckling. In addition, it is also possible to prevent the liquid Q from stagnating when the liquid Q passes through the mouth section 7.

The cap section 73 has a lumen part for containing the valve body 5 therein, and is connected to the tubular section 72 (the valve body installing section 721).

The cap section 73 has therein a first lumen part 731 in which a head section 50 of the valve body 5 to be described later can be inserted, and a fitting part 733 which communicates with the first lumen part 731 and is greater in diameter than the first lumen part 731.

The first lumen part 731 is formed such that its shape corresponds to the outer shape of the head section 50 of the valve body 5.

In addition, the fitting part 733 is a part to be fitted around an outer peripheral portion of the tubular section 72. This ensures that the cap section 73 and the tubular section 72 are connected in a liquid-tight manner, so that the liquid Q inside the mouth section 7 can be prevented from leaking through a gap between the cap section 73 and the tubular section 72. Further, when the cap section 73 and the tubular section 72 are connected together, the first lumen part 731 and the second lumen part 723 communicate with each other and then the first lumen part 731, the second lumen part 723 and the third lumen part 724 forms a space, in which the valve body 5 can be installed.

The cap section 73 has a male screw part 738 at an outer peripheral portion thereof. In the mouth section 7, the male screw part 738 is a part for screw engagement with a female screw part 903 which is formed at an inner peripheral portion of the lock part 902 of the prefilled syringe 90 (see FIGS. 2 and 3).

Incidentally, the material constituting the container body 2A is not specifically restricted. Examples of the material include resin materials such as polyolefins such as polyethylene, polypropylene, cyclic polyethylene, etc.; polyesters such as polyethylene terephthalate, etc.; vinyl resins such as polyvinyl chloride, polyvinyl alcohol, etc.; and other thermoplastic resins, and also may include a combination of two or more of them. In addition, the container body 2A has transparency, for securing visibility of the inside thereof.

The valve body 5 is mounted to (installed in) the mouth section 7. The valve body 5 is formed of an elastic material. Examples of the elastic material include various rubber materials such as silicone rubber, etc. and various thermoplastic elastomers. Use of such an elastic material enables a distal end face 511 of the valve body 5 to have appropriate elasticity. Thus, when the prefilled syringe 90 is connected to the mouth section 7, an end face of the prefilled syringe 90 and the distal end face 511 can make liquid-tight contact with each other (see FIGS. 2 and 3).

The valve body 5 has the tube-like barrel section 55, and the head section 50 integrally provided at one end portion of the barrel section 55.

The head section 50 has a bottomed tube-like shape, and has a lumen part 515 through which the liquid Q and the medicinal liquid R can pass, and a slit (opening/closing part) 512 extending from the flat distal end face 511 to the lumen part 515. The slit 512 has a substantially straight-line-segment-like shape. With the slit 512 formed in such a simple shape, it is ensured that when a pressure is exerted on the distal end face 511 (the vicinity of the slit 512), the distal end face 511 is deformed and, therefore, the slit 512 is opened reliably. In addition, when the pressure is released, the distal end face 511 is restored into its original shape and, hence, the slit 512 is closed assuredly. Thus, the valve body 5 has self-closing property.

In addition, by such an operation of the slit 512, the mouth section 7 can be sealed (see FIG. 1) and unsealed (see FIGS. 2 and 3) easily and reliably.

Also, since the distal end face 511 is flat in shape, in the case of connecting the prefilled syringe 90 thereto, the distal end face 511 (the slit 512) can be preliminarily disinfected easily.

Further, when the above-mentioned pressure is not applied to the head section 50, the head section 50 is inserted in the first lumen part 731 of the cap section 73, and the slit 512 is kept closed.

The barrel section 55 is composed of a bellows-like tubular body. More specifically, the barrel section 55 has a bellows-like outer shape in which larger-diameter ring parts 552 and smaller-diameter ring parts 553 are alternately arrayed along the axial direction. Such a barrel section 55 functions as a deforming section for biasing the head section 50 in the direction for insertion of the head section 50 into the first lumen part 731 of the cap section 73.

Since the barrel section 55 thus functions as a deforming section, it is unnecessary to separately provide the mouth section 7 with a component for constituting a biasing means. This contributes to a reduction in the number of components, and to simplification of structure.

In addition, the barrel section 55 serves most of the function of applying restoring force for restoring the valve body 5 from the barrel section 55 side toward the head section 50 side, but the head section 50 may serve part of the function of applying the restoring force.

A proximal end cap 8A is mounted on a proximal end opening section 26 of the container body 2A. The proximal end cap 8A includes a plate-shaped part 81 covering the proximal end opening section 26, and a fitting part 82 formed at the edge portion of the plate-shaped part 81 along the circumferential direction.

The plate-shaped part 81 is provided with a plurality of through-holes 811 extending therethrough in a thickness direction thereof.

The fitting part 82 has a ring-like shape, and its inside diameter is set to be slightly smaller than the outside diameter of the larger-diameter section 25 of the container body 2A. Thus, the fitting part 82 is fitted around the larger diameter section 25, so that the proximal end cap 8A is securely mounted on the proximal end opening section 26 of the container body 2A and is prevented from being disengaged from the proximal end opening section 26.

Incidentally, the material constituting the proximal end cap 8A is not specifically restricted; for example, such constituent materials as mentioned above in the description of the container body 2A can be used.

As shown in FIGS. 1 to 3, the flexible bag body 3A is disposed inside the container body 2A. The bag body 3A can be reversed by causing the liquid Q (medicinal liquid R) to enter and exit through the mouth section 7. In the vial container 1A of the present embodiment, most part of the bag body 3A is located in the smaller diameter section 24 of the container body 2A in an initial condition (see FIG. 1), and when the liquid Q is injected therein, the bag body 3A is reversed, so that the bag body 3A is positioned in the larger diameter section 25 (see FIG. 2). Thereafter, when the liquid Q (medicinal liquid R) is discharged, the bag body 3A is reversed again so as to be located in the smaller diameter section 24 of the container body 2A (see FIG. 3). The thus-reversible bag body 3A is composed of a film which includes monolayer films of polyolefin resins such as polyethylene, polypropylene, etc., blend resins and copolymer resins containing such polyolefin resin, polyester resins such as polyethylene terephthalate, etc., polyamide resins such as nylon, etc., polyvinylidene chloride, vinyl chloride-polyvinylidene chloride copolymer, etc.; monolayer films obtained by vapordepositing aluminum, silica or the like on the above films; multilayer films obtained by laminating the above monolayer films with other film or metallic foil (e.g., aluminum foil); and so on. Of the films, particularly those which are high in water vapor barrier property and/or oxygen barrier property are preferred.

The bag body 3A is a bag-shaped body including a bottom section 31, and a side section 32 formed integrally with the bottom section 31 at an edge portion of the bottom section 31. Incidentally, the bag body 3A is produced by vacuum forming, air-pressure forming or the like.

In the bag body 3A, an edge part 331 of an opening section 33 thereof is bent outwardly. The thus-bent edge part 331 is fixed to the stepped section 231 (inner peripheral section 23) provided in the vicinity of an intermediate part of the container body 2A in the axial direction, along the circumferential direction. Since the bag body 3A is fixed to the container body 2A in this manner, when the bag body 3A is reversed, the edge part 331 serves as a fulcrum, whereby the reversion is performed easily and reliably. Incidentally, the technique for fixing the bag body 3A is not specifically restricted, and the fixing technique includes adhesion (adhesion with an adhesive or solvent), and welding (thermal welding, RF welding, ultrasonic welding, etc.).

Alternatively, in the bag body 3A, the edge part 331 may be fixed directly to the surface in the vicinity of the intermediate part, in the axial direction, of a container body 2A in which the stepped section 231 is omitted. Further, the bag body 3A may extend from the distal end to the proximal end inside the container body 2A (in which the stepped section 231 is omitted) and may be reversed with the vicinity of the intermediate part thereof as a fulcrum.

As shown in FIG. 1, in the bag body 3A, the thickness t2 of the side section 32 is smaller than the thickness t1 of the bottom section 31. Thus, when the liquid Q is injected therein, the bottom section 31 is substantially not deformed, whereas the side section 32 is reversed sequentially from the vicinity of the edge portion of the bottom section 31 toward the proximal end side, whereby the bag body 3A can be reversed reliably. Further, when the medicinal liquid R is discharged therefrom, the side section 32 is similarly reversed sequentially from the vicinity of the edge portion of the bottom section 31 toward the distal end side, whereby the bag body 3A can be reversed reliably.

Figure 8:
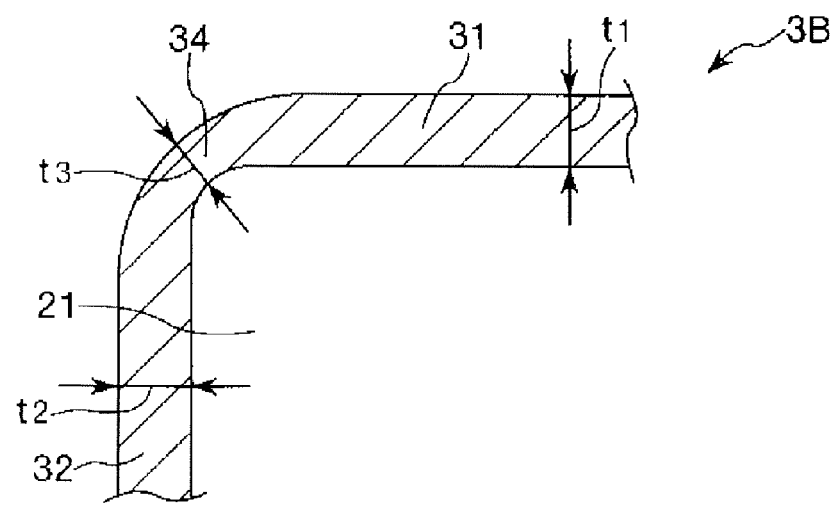
FIG. 8 is an enlarged view of region [B] surrounded by dot-dashed line in FIG. 4.

Incidentally, as shown in FIG. 8, in the bag body 3A, the thickness t1 of the bottom section 31 and the thickness t2 of the side section 32 may be the same. In this case, a boundary section 34 between the bottom section 31 and the side section 32 is preferably formed as a thin section having a thickness smaller than the thicknesses t1 and t2. Thus, the boundary section 34 serves as a flexible part, whereby at the time of reversion of the bag body 3A, the bending direction can be inverted easily, so that the reversion is performed smoothly and assuredly. Alternatively, a material for the bottom section 31 may be harder than a material for the side section 32, and in this case, the reversion can also be achieved similarly.

In addition, the bottom section 31 of the bag body 3A has, at its central portion, a raised section 311 formed by raising the central portion into a dome-like shape. In an initial condition, the raised section 311 is raised toward the proximal end side. Thus, in the initial condition, the containing space 21 with a size necessary for containing the medicine P can be secured. Also, in the case where re-reversion is conducted after the reversion, namely, where the bag body 3A is returned into its initial state, a suction force to such a degree that the medicinal liquid R can be completely discharged from the vial container 1A is exerted, whereby the raising direction of the raised section 311 is inverted into the distal end direction (see FIG. 3). Then, the raised section 311 raised toward the distal end side enters a base part 726 of the mouth section 7. With the entry of the raised section 311, the bottom section 31 of the bag body 3A and the bottom section 22 of the container body 2A are brought into close contact with each other. As a result, the containing space 21 is substantially lost, so that the medicinal liquid R is prevented or restrained from remaining inside the vial container 1A and, therefore, the medicinal liquid R can be completely used, with economy. Incidentally, as shown in FIG. 3, the base part 726 of the mouth section 7 has a tapered portion where the inside diameter gradually decreases toward the distal end side. In addition, the shape of an inside portion of the base part 726 accords with the outer shape of the raised section 311.

Incidentally, because the thickness t1 of the bottom section 31 is large and because of other reasons, the shape of the bag body 3A is easy to maintain, so that the bag body 3A is reversed while maintaining the shape. Thus, the bag body 3A is deformed uniformly in external appearance.

Preferably, the bag body 3A has different colors on the face side and the reverse side, respectively. This makes it possible to visually check whether or not the bag body 3A is in the reversed state.

Next, the state in use of (the method of using) the vial container 1A will be described below.

[1] In the initial state shown in FIG. 1, most part (the other part than the edge part 331) of the bag body 3A is located in the smaller diameter section 24 of the container body 2A. In the initial state, the bottom section 31 of the bag body 3A is separate away from the bottom section 22 of the container body 2A, and the side section 32 is held in close contact with the inner peripheral section 23 of the container body 2A. In this instance, the containing space 21 is surrounded by the bottom section 31 (inclusive of the raised section 311) and the bottom section 22 (inclusive of the mouth section 7).

[2] Next, as shown in FIG. 2, the mouth section 7 of the vial container 1A and the lock part 902 of the prefilled syringe 90 are screw-engaged with each other, to connect the vial container 1A and the prefilled syringe 90 to each other. In this instance, the mouth part 901 of the prefilled syringe 90 presses the valve body 5 in the mouth section 7 of the vial container 1A in the proximal end direction. As a result, the slit 512 in the valve body 5 is put into an open state as above-mentioned, so that the inside of the vial container 1A and the inside of the prefilled syringe 90 communicate with each other.

[3] Subsequently, the plunger of the prefilled syringe 90 is pushed. As a result, the liquid Q inside the prefilled syringe 90 is injected into the vial container 1A through the mouth section 7 of the vial container 1A (see FIG. 2). By the liquid Q thus-injected, the volume of the containing space 21 is increased, and the bottom section 31 of the bag body 3A is pressed toward the proximal end side, so that the bag body 3A is reversed. In this instance, the containing space 21 is surrounded by the bottom section 31 and the side section 32 of the bag body 3A and the bottom section 22 (inclusive of the mouth section 7) and the smaller diameter section 24 of the container body 2A.

When the bag body 3A is thus reversed to increase the volume of the containing space 21, substantially no frictional resistance is generated between the bag body 3A and the container body 2A, so that the liquid Q can be injected therein without any resistive force being felt. Accordingly, the vial container 1A is excellent in operability of injecting the liquid Q therein.

[4] Next, the plunger of the prefilled syringe 90 is reciprocated, to perform a pumping operation. In this instance, also, the bag body 3A is repeatedly reversed, so that substantially no frictional resistance is generated between the bag body 3A and the container body 2A. Thus, the pumping operation can be carried out without any resistive force being felt, that is, with excellent operability. In addition, by this pumping operation, it is possible to obtain the medicinal liquid R in which the medicine P is dissolved uniformly in the liquid Q.

[5] Subsequently, the plunger of the prefilled syringe 90 is pulled. As a result, a suction force is generated in the direction from the containing space 21 of the vial container 1A into the prefilled syringe 90. By the suction force, the medicinal liquid R in the vial container 1A can be sucked into the prefilled syringe 90, and the bag body 3A is reversed in the direction of reducing the volume of the containing space 21 (see FIG. 3). In the thus-reversed bag body 3A, the side section 32 is brought into close contact with the inner peripheral section 23 of the container body 2A. Then, finally, the raised section 311 is inverted.

Also, when the bag body 3A is thus reversed to reduce the volume of the containing space 21, substantially no frictional resistance is generated between the bag body 3A and the container body 2A, so that the liquid Q can be sucked (discharged) without any resistive force being felt. Accordingly, the vial container 1A is excellent in operability at the time of discharging the liquid Q therefrom.

In addition, the amount of the medicinal liquid R sucked can be appropriately controlled according to the amount of pulling of the plunger of the prefilled syringe 90. In the condition shown in FIG. 3, the medicinal liquid R in the containing space 21 is mostly completely sucked.

[6] Next, the vial container 1A and the prefilled syringe 90 are disconnected from each other, and the prefilled syringe 90 is separated from the vial container 1A. Then, the prefilled syringe 90 filled with the medicinal liquid R can be used for administration of the medicinal liquid.

Second Embodiment

Figure 4:
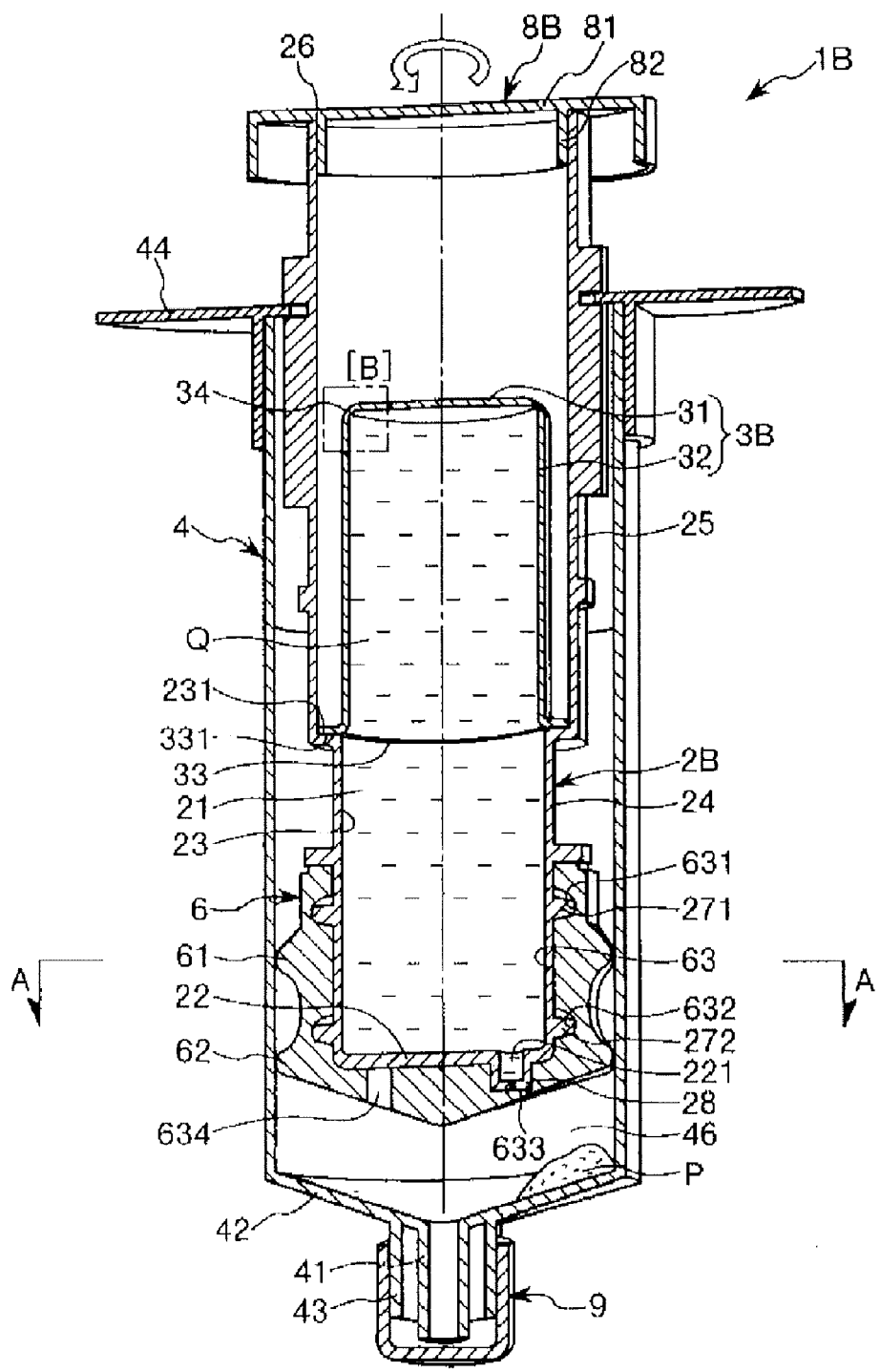
FIG. 4 is a longitudinal sectional view showing an embodiment in the case where a medical container according to the present invention is applied to a syringe (the syringe according to the present invention)
Figure 5:
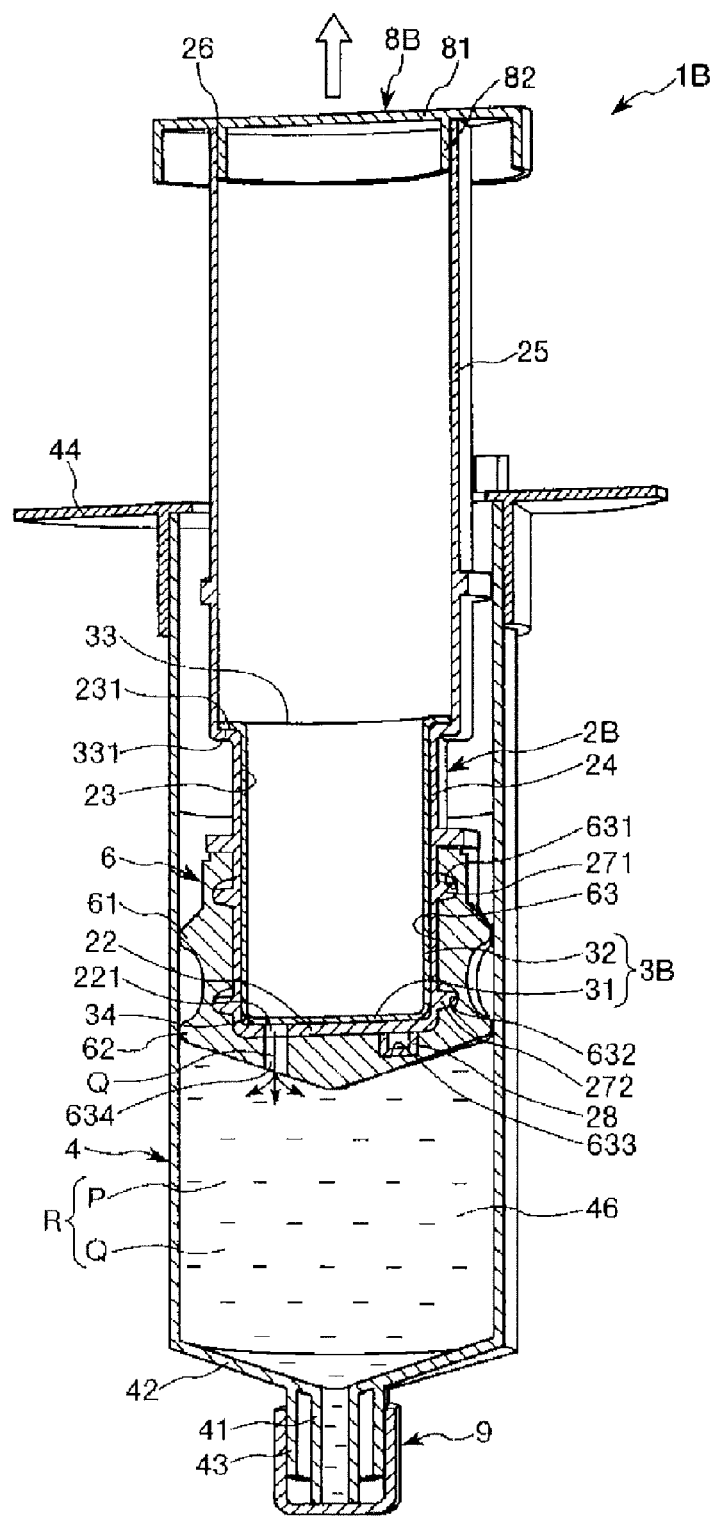
FIG. 5 is a longitudinal sectional view showing the embodiment in the case where the medical container according to the present invention is applied to the syringe (the syringe according to the present invention)
Figure 6:
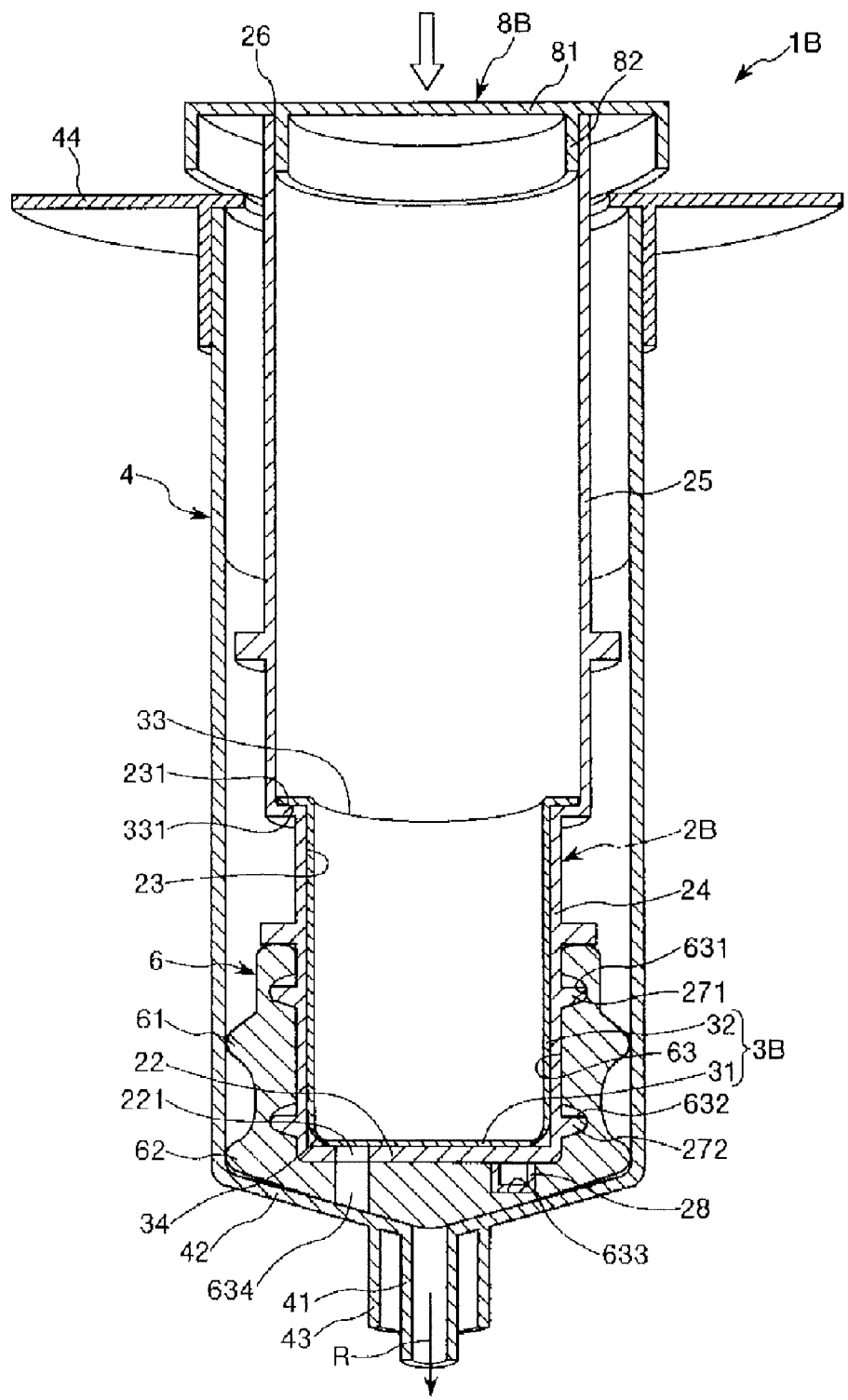
FIG. 6 is a longitudinal sectional view showing the embodiment in the case where the medical container according to the present invention is applied to the syringe (the syringe according to the present invention)
Figure 7:
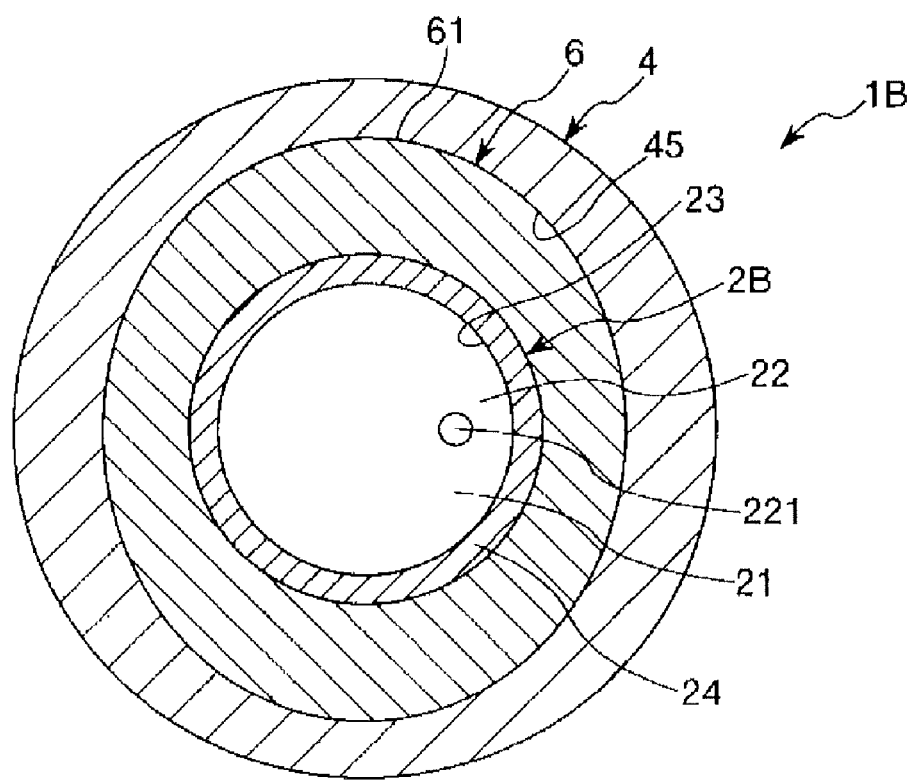
FIG. 7 is a sectional view taken along line A-A of FIG. 4.

FIGS. 4 to 6 are longitudinal sectional views showing an embodiment in the case where the medical container according to the present invention is applied to a syringe (the syringe according to the present invention). FIG. 7 is a sectional view taken along line A-A of FIG. 4, and FIG. 8 is an enlarged view of region [B] surrounded by dot-dash line in FIG. 4. Incidentally, in the following, for convenience of description, the upper side in FIGS. 4 to 6 will be referred to as "proximal end side," and the lower side as "distal end side."

Now, with reference to the drawings, a second embodiment of the medical container and the syringe according to the present invention will be described below. The following description will be made to center on differences from the above-mentioned embodiment, and descriptions of the same items as above will be omitted.

The present embodiment is the same as the first embodiment, except for difference in application of the medical container.

A syringe (medical container) 1B shown in FIGS. 4 to 6 is a two-chamber type prefilled syringe wherein a medicine P and a liquid Q for dissolving the medicine P are preliminarily contained separately in two chambers inside the syringe. The syringe 1B includes an outer tube (syringe outer tube) 4, a gasket 6 slidable inside the outer tube 4, an inner tube 2B mounted on the gasket 6, a bag body 3B disposed in the inner tube 2B, a distal end cap 9 detachably mounted on a mouth section 41 of the outer tube 4, and a proximal end cap 8B mounted on a proximal end opening section 26 of the inner tube 2B.

The outer tube 4 is composed of a bottomed tube-like member having a bottom section 42 on the distal end side. As shown in FIG. 7, an intermediate portion of the outer tube 4 is elliptic in cross-sectional shape of an inner peripheral section thereof. At this position, the gasket 6 also has an outer peripheral section restricted to be elliptic in shape. Thus, when the inner tube 2B is rotated about its axis relative to the outer tube 4 as will be described later (see FIG. 4), the gasket 6 is prevented from being rotated together with the inner tube 2B, and only the inner tube 2B can be rotated.

At a central portion of the bottom section 42 of the outer tube 4, the mouth section 41 having a diameter smaller than that of a barrel section of the outer tube 4 is integrally formed in a projecting manner. To the mouth section 41, there is fitted or mounted, for example, a needle hub, a connector, a tube or the like (not shown) when the syringe is put to use.

In addition, on the outer peripheral side of the mouth section 41, a cap mounting section 43 disposed concentrically with the mouth section 41 is formed in a projecting manner. The cap mounting section 43 has a ring-like shape, and the distal end cap 9 is detachably mounted on an outer peripheral section thereof.

Further, a flange 44 is formed at the outer periphery of the proximal end of the outer tube 4. At the time of, for example, moving the inner tube 2B relative to the outer tube 4, the operation can be carried out with a finger or fingers put on the flange 44. In addition, the outer tube 4 is provided with graduations for measurement.

The material constituting the outer tube 4 is not specifically restricted. Examples of the material include resin materials such as polyolefins such as polyethylene, polypropylene, cyclic polyethylene, etc.; polyesters such as polyethylene terephthalate, etc.; vinyl resins such as polyvinyl chloride resin, polyvinyl alcohol, etc.; and other thermoplastic resins, and also may include a combination of two or more of them. Besides, the container body 2A has transparency, for securing visibility of the inside thereof.

To the cap mounting section 43 of the outer tube 4, the distal end cap 9 is mounted by fitting. The distal end cap 9 is a seal member for sealing the mouth section 41.

The distal end cap 9 has a cup-like shape, and its inside diameter is set to be slightly smaller than the outside diameter of the cap mounting section 43. Thus, the distal end cap 9 is fitted and mounted on the cap mounting section 43 reliably, and, when the distal end cap 9 is pulled in the distal end direction, the fitting is released, and the distal end cap 9 is detached from the cap mounting section 43.

The material constituting the distal end cap 9 is not particularly limited. For example, such constituent materials as mentioned above in the description of the outer tube 4 can be used.

Incidentally, the technique for sealing the mouth section 41 is not limited to the technique by use of the distal end cap 9. For example, the sealing may be carried out by an elastic plug, adhesion of a film, or the like.

The gasket 6 made of an elastic material is inserted in the outer tube 4. At an outer peripheral section of the gasket 6, a plurality of ring-shaped projected parts 61 and 62 projecting outward are formed along the whole circumference. The projected parts 61 and 62 are slid while keeping close contact with the inner peripheral section 45 of the outer tube 4, whereby liquid-tightness can be maintained more reliably, and slidability thereof can be improved.

In the present embodiment, the two projected parts 61 and 62 are formed along the axial direction of the gasket 6. More specifically, the projected parts 61 and 62 are formed respectively at an intermediate portion (central portion) in the axial direction and at a distal end portion of the gasket 6. Of these projected parts, the projected part 62 has, on a distal end side thereof, a tapered surface where the outside diameter gradually decreases toward the distal end.

Incidentally, in the present invention, the position, number, sectional shape, etc. of the projected parts 61 and 62 are not restricted to the above-mentioned.

In addition, the gasket 6 has a cavity section 63 which is open on the proximal end surface thereof. In the cavity section 63, a distal end portion of the inner tube 2B is inserted. The cavity section 63 has an inner peripheral section where rotational support portions 631 and 632 for rotatably supporting the inner tube 2B are formed at two intermediate positions in the axial direction thereof. The rotational support portions 631 and 632 are each composed of an enlarged diameter portion where the inside diameter of the cavity section 63 is enlarged, and ribs 271 and 272 of the inner tube 2B which will be described later are inserted in the rotational support portions 631 and 632.

The elastic material constituting the gasket 6 is not specifically restricted. Examples of the material include various rubber materials such as natural rubber, isoprene rubber, butadiene rubber, styrene-butadiene rubber, etc., and various thermoplastic elastomers based on styrene, polyolefin or the like, and also may include combinations of two or more of them.

Further, as shown in FIG. 4, the syringe 1B gastightly contains an appropriate amount of a medicine P in a distal-end-side space 46 surrounded by the outer tube 4 and the gasket 6.

The inner tube 2B with the gasket 6 mounted thereon is inserted into the outer tube 4. The inner tube 2B functions as a plunger which is operated to move the gasket 6, and also functions as a container for containing the liquid Q.

The inner tube 2B has a bottomed tube-like shape, and has a mouth section 221 at a bottom section 22 (distal end portion) thereof. The mouth section 221 is composed of a through-hole piercing the bottom section 22 in the thickness direction. Through the mouth section 221, the inside of the inner tube 2B (the containing space 21) and the distal-end-side space 46 communicate with each other, and the liquid Q can flows out toward (enter and exit) the distal-end-side space 46 (see FIG. 5).

In addition, in the initial condition shown in FIG. 4, the mouth section 221 of the inner tube 2B is sealed with a breakable communicating section 28. The breakable communicating section 28 is formed integrally with the bottom section 22 of the inner tube 2B in a projecting manner.

Besides, as shown in FIG. 5, the breakable communicating section 28 is configured so as to be broken when the inner tube 2B is rotated about its axis. By the breakage, the mouth section 221 is unsealed, and the interior of the inner tube 2B and the distal-end-side space 46 communicate with each other through the unsealed mouth section 221.

Thus, the breakable communicating section 28 is a part which functions as an opening/closing means for opening and closing the mouth section 221 and thereby switching between communication and non-communication between the inside of the inner tube 2B and the distal-end-side space 46.

Incidentally, the cavity section 63 of the gasket 6 has, at a bottom portion thereof, a recessed insertion section 633 into which to insert the breakable communicating section 28. Since the breakable communicating section 28 is inserted in the insertion section 633, when the inner tube 2B is rotated, the breakable communicating section 28 is subjected to a shear stress, and when the shear stress excesses a breaking limit, the breakable communicating section 28 is broken. Then, the breakable communicating section 28 is broken into a broken piece, which remains inside the insertion section 633 (see FIG. 5).

In addition, the cavity section 63 of the gasket 6 has a through-hole 634 in the bottom portion and at a position different from the position of the insertion section 633. The through-hole 634 is a part for permitting the inside of the inner tube 2B and the distal-end-side space 46 to communicate with each other therethrough, together with the opened mouth section 221 (see FIG. 5).

As shown in FIGS. 1 to 3, in the inner tube 2B, the stepped section 231, the inside diameter of which changes abruptly, is formed at an intermediate position of the inner peripheral section 23. The stepped section 231 serves as a fixing portion at which the bag body 3B is fixed. In addition, the inner tube 2B is divided into a smaller diameter section 24 on the distal-end side and a larger diameter section 25 on the proximal-end side, by the stepped section 231.

Incidentally, the material constituting the inner tube 2B is not specifically restricted. For example, such constituent materials as mentioned above in the description of the outer tube 4 can be used. Besides, the inner tube 2B has transparency, for securing visibility of the inside thereof.

The proximal end cap 8B is mounted on the proximal end opening section 26 of the inner tube 2B. The proximal end cap 8B includes a circular disk-like plate-shaped part 81 covering the proximal end opening section 26, and a fitting part 82 which is disposed concentrically with the plate-shaped part 81 and is formed along the circumferential direction.

The fitting part 82 has a ring-like shape, and has an outside diameter which is set to be slightly greater than the inside diameter of the larger diameter section 25 of the inner tube 2B. Thus, the fitting part 82 is fitted into the larger diameter section 25, so that the proximal end cap 8B is reliably mounted on the proximal end opening section 26 of the inner tube 2B, and is prevented from being disengaged from the proximal end opening section 26.

Incidentally, the material constituting the proximal end cap 8B is not particularly limited. For example, such constituent materials as mentioned above in the description of the outer tube 4 can be used.

As shown in FIGS. 4 to 6, the flexible bag body 3B is disposed inside the inner tube 2B. A containing space 21 surrounded by the bag body 3B and the inner tube 2B is filled with the liquid Q.

The bag body 3B can be reversed by flowing-out of the liquid Q through the mouth section 221. In the syringe 1B according to the present embodiment, the bag body 3B is located in the larger diameter section 25 of the inner tube 2B in the initial state (see FIG. 4), and, upon suction of the liquid Q into the distal-end-side space 46, the bag body 3B is reversed to be located in the smaller diameter section 24 (see FIG. 5). The bag body 3B being reversible in this manner can be formed from such constituent materials as mentioned in the first embodiment.

The bag body 3B is a bag-like body which includes a bottom section 31, and a side section 32 formed integrally with the bottom section 31 at an edge portion of the bottom section 31.

The bag body 3B has an edge part 331 of an opening section 33 thereof, the edge part 331 being bent outwardly. The thus-bent edge part 331 is fixed to the stepped section 231 (inner peripheral section 23) of the inner tube 2B, along the circumferential direction of the stepped section 231. Since the bag body 3B is fixed to the inner tube 2B in this manner, when the bag body 3B is reversed, the edge part 331 serves as a fulcrum, whereby the reversion thereof is performed easily and reliably. Incidentally, the technique for fixing the bag body 3B is not specifically restricted, and examples of the fixing technique include adhesion (adhesion with an adhesive or solvent), and welding (thermal welding, RF welding, ultrasonic welding, etc.).

As shown in FIG. 8, in the bag body 3B, the thickness t1 of the bottom section 31 and the thickness t2 of the side section 32 are the same. In addition, a boundary section 34 between the bottom section 31 and the side section 32 is a thin section having a thickness t3 smaller than the thicknesses t1 and t2. Thus, similarly to the first embodiment described above, the reversion is performed smoothly and reliably.

As shown in FIGS. 5 and 6, in the bag body 3B reversed, the bottom section 31 is brought into close contact with the bottom section 22 of the inner tube 2B, and the side section 32 is brought into close contact with the smaller diameter section 24 (inner peripheral section 23) of the inner tube 2B. As a result, the containing space 21 is substantially lost, so that the medicinal liquid R is prevented or restrained from remaining inside the containing space 21 and, therefore, the medicinal liquid R can be completely used, with economy.

Incidentally, the bottom section 31 of the bag body 3B may have a raised section similar to the raised section 311 formed on the bag body 3A of the first embodiment. This makes it possible to more reliably prevent the medicinal liquid R from remaining in the containing space 21.

In addition, the bag body 3B may have different colors on the face side and the reverse side thereof, respectively. This makes it possible to check whether or not the bag body 3B is in the reversed state.

Next, the state in used of (the method of using) the syringe 1B will be described below.

[1] In the initial state shown in FIG. 4, the bag body 3B is located in the larger diameter section 25 of the inner tube 2B. In this instance, the containing space 21 is surrounded by the bottom section 31 and the side section 32 of the bag body 3B and the bottom section 22 and the smaller diameter section 24 of the inner tube 2B. Besides, the containing space 21 is filled with the liquid Q.

In addition, in the state shown in FIG. 4, the side section 32 of the bag body 3B is spaced from the larger diameter section 25 (inner peripheral section 23) of the inner tube 2B. Thus, at the time when the bag body 3B is reversed, the side section 32 is easy to deform, so that an operation of pulling the inner tube 2B to be described later can be carried out easily.

Further, as above-mentioned, in the initial condition, the mouth section 221 of the inner tube 2B is sealed with the breakable communicating section 28. Thus, even if the inner tube 2B is unwillingly pulled in the proximal direction relative to the outer tube 4, a suction force arising from an increase in the volume of the distal-end-side space 46 can be prevented from affecting the containing space 21. As a result, the liquid Q in the containing space 21 is prevented from unwillingly flowing out into the distal-end-side space 46.

[2] Next, the inner tube 2B is rotated about its axis relative to the outer tube 4. As a result, the breakable communicating section 28 is broken as above-mentioned, so that the mouth section 221 is opened. Incidentally, this rotating operation is performed until the mouth section 221 is displaced so as to align with the through-hole 634 in the gasket 6 (see FIG. 5). In order that the mouth section 221 and the through-hole 634 can be aligned with each other in this manner, it is preferable to provide, for example, a marker or a positioning mechanism. Incidentally, the rotating angle in the rotating operation is not particularly limited, and for example, the rotating angle is preferably in the range from 60 to 180 degrees, more preferably 60 to 90 degrees.

[3] Subsequently, as shown in FIG. 5, the inner tube 2B is pulled in the proximal end direction relative to the outer tube 4. This increases the volume of the distal-end-side space 46, so that pressure inside the distal-end-side space 46 is reduced, and a suction force for sucking the liquid Q from the inside of the containing space 21 is generated. By the suction force, the liquid Q in the containing space 21 is caused to flow sequentially through the mouth section 221 of the inner tube 2B and the through-hole 634 in the gasket 6 into the distal-end-side space 46, and the bag body 3B is reversed. Besides, this pulling operation is conducted until the containing space 21 is substantially lost, that is, until the liquid Q completely flows out of the containing space 21.

When the bag body 3B is thus reversed to decrease the volume of the containing space 21, substantially no frictional resistance is generated between the bag body 3B and the inner tube 2B, so that the liquid Q can be discharged without any resistive force being felt. Accordingly, the syringe 1B is excellent in operability at the time of discharging the liquid Q.

[4] Next, the syringe 1B is shaken to dissolve the medicine P in the liquid Q. As a result, the medicinal liquid R containing the medicine P dissolved uniformly in the liquid Q can be obtained.

Incidentally, other than the shaking of the syringe 1B, a pumping operation of reciprocating the inner tube 2B in its axial direction relative to the outer tube 4 may be performed. In the case of the pumping operation, also, the bag body 3B is reversed repeatedly, so that substantially no frictional resistance is generated between the bag body 3B and the inner tube 2B. Accordingly, excellent operability in the pumping operation is obtained.

[5] After the medicine P is dissolved in the liquid Q, an operation reverse to the rotating operation conducted in the above [2] is performed, whereby a route for the liquid Q to return into the bag body 3B through the mouth section 221 is block off. Then, the distal end cap 9 is detached from the distal end of the mouth section 41 to release the sealing (see FIG. 6), and air is vented from the inside of the distal-end-side space 46.

Thereafter, for example, a connector, a tube, a needle hub or the like (not shown) is attached to the mouth section 41.

Then, as shown in FIG. 6, the inner tube 2B is pushed in the distal end direction relative to the outer tube 4. As a result, the gasket 6 is slid inside the outer tube 4 in the distal end direction, whereby the medicinal liquid R in the distal-end-side space 46 is delivered (discharged) to the above-mentioned connector, tube, or needle hub or the like.

Incidentally, when the inner tube 2B is pushed, the mouth section 221 can be sealed again at an arbitrary position on the bottom part of the cavity section 63 of the gasket 6, by rotating the inner tube 2B. The arbitrary position may be any place as long as the mouth section 221 can be sealed, for example, the part at which the breakable communicating section 28 is located, or a part different from the above part.

While the medical container and the syringe according to the present invention have been described above with reference to the embodiments shown in the drawings, the invention is not restricted to these embodiments, and each of the components of the medical container and the syringe can be replaced with a constituent element that can exhibit an equivalent function. Further, arbitrary constituent elements may be added.

In addition, the medical container according to the present invention may be one that is obtained by combining arbitrary two or more constituent elements (characteristic features) of the above-described embodiments.

INDUSTRIAL APPLICABILITY

According to the present invention, when a liquid is injected into the space through the mouth section of the tube body, the bag body is pressed in the proximal end direction by the liquid, so that the bag body is reversed. In this instance, the volume of the space is increased, and then the liquid flows into the containing space (the containing space is filled with the liquid). When the bag body is thus reversed to increase the volume of the containing space, substantially no frictional resistance is generated between the bag body and the tube body, so that the liquid can be injected therein without any resistive force being felt. Accordingly, the present invention offers excellent operability in injecting the liquid thereinto.

In addition, when the liquid within the space is sucked, the bag body is consequently reversed in such a direction that the volume of the space is reduced. Also, when the bag body is thus reversed to decrease the volume of the space, substantially no frictional resistance is generated between the bag body and the tube body, so that the liquid can be discharged without any resistive force being felt. Accordingly, the present invention also offers excellent operability in discharging the liquid therefrom.

Further, where the raised section is provided, the space is substantially lost upon discharge of the liquid, so that the liquid is prevented or restrained from remaining in the space, and, therefore, the liquid can be completely used without wasting any liquid.

Therefore, the present invention has industrial applicability.

The invention claimed is:

1. A medical container comprising:
    a tube body having, at a distal end portion thereof, a mouth section through which a liquid can enter and exit;
    a bag body which is disposed inside the tube body and which is flexible and reversible;
    the bag body possessing oppositely located axial ends, one axial end being an open axial end and the other axial end being a closed axial end, the closed axial end possessing a first surface facing towards the mouth section and an oppositely facing second surface facing away from the mouth section, the bag body possessing an edge at the open axial end that is fixed to the tube body at a fulcrum;
    medicine positioned between the first surface of the closed axial end of the bag body and the mouth section when the closed axial end of the bag body is at a position on one side of the fulcrum and before liquid enters through the mouth section;
    wherein when a liquid enters through the mouth section, the liquid mixes with the medicine and the bag body is reversed about the fulcrum to increase the volume of a space surrounded by the tube body and the bag body by virtue of the closed axial end of the bag body axially moving from the position on the one side of the fulcrum to a position on an opposite side of the fulcrum, the one side of the fulcrum being located closer to the mouth section than the opposite side of the fulcrum; and
    wherein when the liquid exits through the mouth section, the bag body is reversed about the fulcrum so as to decrease the volume of the space surrounded by the tube body and the bag body by virtue of the closed axial end of the bag body axially moving from a position on the opposite side of the fulcrum to a position on the one side of the fulcrum.

2. The medical container according to claim 1, wherein the fulcrum is at an intermediate part in the axial direction inside the tube body.

3. The medical container according to claim 2,
    wherein the bag body has a bottom section and a side section integrally formed at an edge portion of the bottom section; and
    wherein when the bag body is reversed, the side section is brought into close contact with a portion of the tube body that is positioned on the distal end side of the medical container relative to the fulcrum.

4. The medical container according to claim 3, wherein the thickness of the side section is smaller than the thickness of the bottom section and/or the material of the bottom section is harder than the material of the side section.

5. The medical container according to claim 3, wherein a flexible relatively thin section is formed at a boundary section between the bottom section and the side section, the flexible relatively thin section being thinner than the bottom section and the side section.

6. The medical container according to claim 1, wherein the bag body has a raised section which is inverted and then enters the mouth section when the liquid flows out through the mouth section.

7. A medical container comprising:
    a tube body possessing a distal end portion, a proximal end portion and an intermediate part between the distal and proximal end portions, the tube body possessing an interior and including a sealed mouth section that is openable and through which liquid enters and exits the interior of the tube body when the mouth section is open, the mouth section being located at the distal end portion of the tube body;
    a flexible and reversible bag body positioned inside the tube body, the bag body being reversible inside the tube body about a fulcrum located at the intermediate part of the tube body;
    wherein liquid exiting the tube body through the mouth section causes the reversible and flexible bag body to be reversed about the fulcrum so that the bag body moves from one side of the fulcrum to an opposite side of the fulcrum to change a volume of a space surrounded by the tube body and the bag body;
    a gasket mounted on the distal end portion of the tube body;
    an outer tube in which both the tube body and the gasket are positioned to be movable in an axial direction of the outer tube, the gasket being in liquid-tight contact with an inner surface of the outer tube, the portion of the gasket that is in liquid-tight contact with the inner surface of the outer tube axially overlapping a distal end portion of the interior of the tube body that is positioned proximal of the sealed mouth section; and
    wherein the space is configured to communicate, through the mouth section when the mouth section is open, with a distal-end-side space surrounded by the outer tube and the gasket.

8. The medical container according to claim 7,
    wherein the bag body includes a bottom section possessing an edge section, the body bag also including a side section integrally formed at the edge portion of the bottom section and extending away from the bottom section; and
    wherein when the bag body is reversed, the side section is brought into close contact with a portion of the tube body that is positioned on the distal end side of the fulcrum.

9. The medical container according to claim 8, wherein the side section of the bag body possesses a thickness smaller than the thickness of the bottom section of the bag body and/or the material of the bottom section is harder than the material of the side section.

10. The medical container according to claim 8, wherein the bag body includes a flexible relatively thin section at a boundary section between the bottom section and the side section, the flexible relatively thin section being thinner than the bottom section and the side section.

11. The medical container according to claim 7, wherein the bag body includes a raised section which is inverted and then enters the mouth section when the liquid exits out through the mouth section.

12. A medical container comprising:
a tube body possessing a distal end portion and an interior, the tube body including a sealed mouth section that is openable and through which liquid enters and exits the interior of the tube body, the mouth section being located at the distal end portion of the tube body;
a flexible and reversible bag body positioned inside the tube body, the bag body being reversible inside the tube body about a fixed fulcrum, the bag body including a bottom section extending across the bag body;
a containing space surrounded by the tube body and the bag body; the containing space containing a liquid;
the reversible and flexible bag body being configured to be reversed from a position in which the bottom section of the bag body is on one axial side of the fixed fulcrum to a position in which the bottom section of the bag body is on an opposite axial side of the fulcrum to decrease a volume of the containing space when the liquid in the containing space exits the containing space by way of the open mouth section;
a gasket mounted on the distal end portion of the tube body;
an outer tube in which both the tube body and the gasket are positioned to be axially movable relative to the outer tube, the gasket being in liquid-tight contact with an inner surface of the outer tube, the portion of the gasket that is in liquid-tight contact with the inner surface of the outer tube axially overlapping a distal end portion of the interior of the tube body that is positioned proximal of the sealed mouth section; and
wherein the space is configured to communicate, through the mouth section when the mouth section is open, with a distal-end-side space surrounded by the outer tube and the gasket.

13. The medical container according to claim 12, wherein an end portion of the bag body is fixed to a portion of the tube body in the interior of the tube body.

14. The medical container according to claim 12, wherein the section possesses an edge portion, the body bag also including a side section integrally formed at the edge portion of the bottom section and extending away from the bottom section; and wherein when the bag body is reversed, the side section is brought into close contact with a portion of the tube body that is positioned on the distal end side of the fulcrum.

15. The medical container according to claim 14, wherein the side section of the bag body possesses a thickness smaller than the thickness of the bottom section of the bag body and/or the material of the bottom section is harder than the material of the side section.

16. The medical container according to claim 14, wherein the bag body includes a flexible relatively thin section at a boundary section between the bottom section and the side section, the flexible relatively thin section being thinner than the bottom section and the side section.

17. The medical container according to claim 12, wherein the bag body includes a raised section which is inverted and then enters the mouth section when the liquid exits out through the mouth section.

* * * * *

UNITED STATES PATENT AND TRADEMARK OFFICE
CERTIFICATE OF CORRECTION

| | | |
|---|---|---|
| PATENT NO. | : 9,155,679 B2 | Page 1 of 1 |
| APPLICATION NO. | : 13/265522 | |
| DATED | : October 13, 2015 | |
| INVENTOR(S) | : Masaomi Imai et al. | |

It is certified that error appears in the above-identified patent and that said Letters Patent is hereby corrected as shown below:

In the claims
Column 18, line 15, Claim 14, change: "the section possesses an edge portion" to -- the bottom section possesses an edge portion --.

Signed and Sealed this
Twenty-ninth Day of March, 2016

Michelle K. Lee
*Director of the United States Patent and Trademark Office*